(12) United States Patent
Woodard

(10) Patent No.: US 7,862,501 B2
(45) Date of Patent: Jan. 4, 2011

(54) SYSTEM FOR PREVENTING DIASTOLIC HEART FAILURE

(75) Inventor: John Campbell Woodard, Turramurra (AU)

(73) Assignee: Thoratec Corporation, Pleasanton, CA (US)

( * ) Notice: Subject to any disclaimer, the term of this patent is extended or adjusted under 35 U.S.C. 154(b) by 508 days.

(21) Appl. No.: 11/726,383

(22) Filed: Mar. 21, 2007

(65) Prior Publication Data
US 2007/0238915 A1    Oct. 11, 2007

(30) Foreign Application Priority Data
Mar. 23, 2006    (AU) .............................. 2006901498

(51) Int. Cl.
*A61N 1/362* (2006.01)
(52) U.S. Cl. ...................................................... 600/19
(58) Field of Classification Search .................. 600/16, 600/17; 604/7, 9, 43
See application file for complete search history.

(56) References Cited

U.S. PATENT DOCUMENTS

| | | | |
|---|---|---|---|
| 5,289,821 A | 3/1994 | Swartz | |
| 6,027,498 A | 2/2000 | Mutch et al. | |
| 6,066,086 A | 5/2000 | Antaki et al. | |
| 6,071,093 A | 6/2000 | Hart | |
| 6,227,797 B1 | 5/2001 | Watterson et al. | |
| 6,264,601 B1 | 7/2001 | Jassawalla et al. | |
| 6,277,078 B1 | 8/2001 | Porat et al. | |
| 6,367,333 B1 | 4/2002 | Bullister et al. | |
| 6,395,026 B1* | 5/2002 | Aboul-Hosn et al. ....... 623/3.13 |
| 6,623,420 B2 | 9/2003 | Reich et al. | |
| 6,945,998 B2 | 9/2005 | Liotta | |
| 6,991,595 B2 | 1/2006 | Burke et al. | |
| 7,138,776 B1 | 11/2006 | Gauthier et al. | |
| 7,645,225 B2* | 1/2010 | Medvedev et al. ............ 600/17 |
| 2001/0009645 A1 | 7/2001 | Noda | |
| 2002/0183628 A1 | 12/2002 | Reich et al. | |
| 2005/0107658 A1* | 5/2005 | Brockway ..................... 600/16 |
| 2005/0208095 A1* | 9/2005 | Hunter et al. ............... 424/423 |
| 2006/0149331 A1* | 7/2006 | Mann et al. ................... 607/34 |

FOREIGN PATENT DOCUMENTS

| | | |
|---|---|---|
| EP | 1 354 606 | 10/2003 |
| JP | 2005-66013 | 3/2005 |
| WO | WO99/59652 | 11/1999 |

(Continued)

OTHER PUBLICATIONS

Australian Patent Office International-Type Search Report.

(Continued)

*Primary Examiner*—George Manuel
*Assistant Examiner*—Robert N Wieland
(74) *Attorney, Agent, or Firm*—Squire, Sanders & Dempsey L.L.P.

(57) ABSTRACT

A pumping system for assisting the circulatory system of a patient, wherein the system includes a rotary flow blood pump by a first cannula connected to a portion of the left side of the heart and a second cannula connected to the aorta; and characterised in that the pumping speed of said pump is adjusted in accordance with measurements from a pressure sensor mounted in or on an inner wall of a portion of the left side of the heart.

8 Claims, 5 Drawing Sheets

FOREIGN PATENT DOCUMENTS

WO     WO 01/05023     1/2001

OTHER PUBLICATIONS

Antaki, Boston, Simaan, Control of Heary Assist Devices.

Boston, Simaan, Antaki, Yu, Choi, Intelligent Control Design for Heart Assist Devices.

Hahn, Schob, Determining Flow & Pressure in a Bearingless Pump From the Position Signals &.

Boening, Friedrich, Caliebe, Cremer, Efficacy of Intracardiac Right Ventricular Microaxial Pump Support During Beathing Heart Surgery.

Lucke, Griewski, Koch, On the Utilization of Automatic Control Systems Within a Perfusion System.

* cited by examiner

SYSTEM FOR PREVENTING DIASTOLIC HEART FAILURE

FIELD OF THE INVENTION

The present invention relates an improved system for assisting the circulatory system of patient and wherein said system may allow preventing of conditions that require controlled depressurisation of the heart.

BACKGROUND OF THE INVENTION

Previously, left ventricular assist devices have been commonly used to assist the heart pump blood. Current generations of the left ventricular assist devices included rotary blood pumps that were a significant improvement beyond the previous versions of pulsatile pumps, which relied on compression pusher plates or pneumatic drive systems cooperating with one-way valves to provide a pulsatile blood flow. The main advantage for rotary blood pumps is that they are typically considerably smaller and include less points or areas of stagnant blood flow, and thereby may reduce or avoid the risk of haemolysis or the formation of blood clots.

The rotary blood pumps typically provide a relatively continuous flow output by way of a centrifugal or axial type impeller, which is electrically urged to rotate within a housing to provide the pumping force. These continuous flow pumps generally are connected in parallel with the heart of a patient. This parallel flow is typically made possible by connecting the rotary blood pump to the apex of the ventricle through a cored hole and then pumping the blood to a cannulated area of the aorta or pulmonary artery.

One of the main disadvantages of these rotary blood pumps is that the output flow is relatively continuous and the output of the natural heart is pulsatile thus it is difficult to control pressures within the heart using rotary pumps. Furthermore, rotary pumps generally do not intrinsically change their pumping activity sufficiently in response to normal changes in blood flow. In some instances where inflow to the heart is transiently reduced, blood is effectively being sucked out of the ventricle at a rate faster than the filling rate of the ventricle. This generally results in the ventricle suffering a suction event whereby the interventricular septum and free wall are pulled together. This pulling together of the septum and the ventricle wall may partially or fully occlude the inflow cannula of the rotary blood pump, thereby stopping or limiting flow from both the natural heart and the rotary blood pump. This reduction in ventricular pressure can also cause collapse of the heart's atria or the veins supplying the heart, similarly reducing the amount of blood able to be pumped. In addition, gross disturbance of the shape of the ventricle can lead to dangerous cardiac arrhythmias. Thus, these suction events preferably should be avoided.

Furthermore, in cases of diastolic heart failure, stiffening of the ventricular wall may impede the filling of the heart and thus require higher effective filling pressures to achieve normal ventricular volumes. In this condition, even marginal mismatches between the amount of blood being pumped by the blood pump and the amount arriving at the heart can cause dangerous rises in venous pressure resulting in life-threatening congestion of either the lungs or systemic veins.

An example of a rotary blood pump is described within U.S. Pat. No. 6,227,797—Watterson et al. This rotary blood pump is a generally centrifugal device utilising a hydrodynamic suspension to levitate a magnetically rotated impeller.

Previously, U.S. Pat. No. 6,945,998—Liotta et al described a pulsatile blood pump connected between the left atrium of a heart and the aorta. However, the blood pump described in this specification is a pulsatile pump, which includes two mechanical valves and a system of pusher plates. The combined result of these features is that there are multiple possible stagnation points for blood clots to be formed within the described pulsatile pump.

Furthermore, pulsatile pumps are generally incapable of generating significant suction events in the natural heart. Rotary blood pumps work in a mechanically different manner and generally may induce suction events.

The present invention aims to or at least address or ameliorate one or more of the disadvantages associated with the abovementioned prior art.

BRIEF DESCRIPTION OF THE INVENTION

According to a first aspect the present invention consists in a pumping system for assisting the circulatory system of a patient, wherein said system includes: a rotary flow blood pump by a first cannula connected to a portion of the left side of the heart and a second cannula connected to the aorta; and characterised in that the pumping speed of said pump is adjusted in accordance with measurements from a pressure sensor mounted in or on an inner wall of a portion of the left side of the heart.

Preferably the pump maintains a predetermined blood pressure profile and range within the left atrium.

Preferably the pump maintains a predetermined blood pressure profile and range within the left ventricle.

Preferably said pressure sensor is mounted in the left atrium or the left atrial appendage.

Preferably a portion of the left side of the heart is stented to prevent or limit collapse.

Preferably said rotary blood pump is implanted within the body of a patient.

According to a second aspect the present invention consists in a pumping system for assisting the circulatory system of a patient, said system includes: a rotary flow blood pump adapted to be connected to a portion of the left side of the heart of said patient by a first cannula and adapted to be connected to the aorta of said heart by a second cannula; and wherein the pumping speed of said pump is adjusted in accordance with measurements from a pressure sensor adapted to be mounted in or on an inner wall of a portion of the left side of said heart.

According to a third aspect the present invention consists in a pumping system for assisting the circulatory system of a patient, said system comprising a left ventricle assist device adapted to be fitted in parallel to the heart of said patient, and a pressure sensor adapted to be mounted in or on an inner wall of a portion of the left side of said heart remote from said left ventricle assist device, and wherein the speed of said pump is adjusted in response to measurements from said pressure sensor.

BRIEF DESCRIPTION OF THE DRAWINGS

Embodiments of the present invention will now be described with reference to the accompanying drawings wherein.

BRIEF DESCRIPTION OF THE PREFERRED EMBODIMENTS AND PRIOR ART

Figure 1:
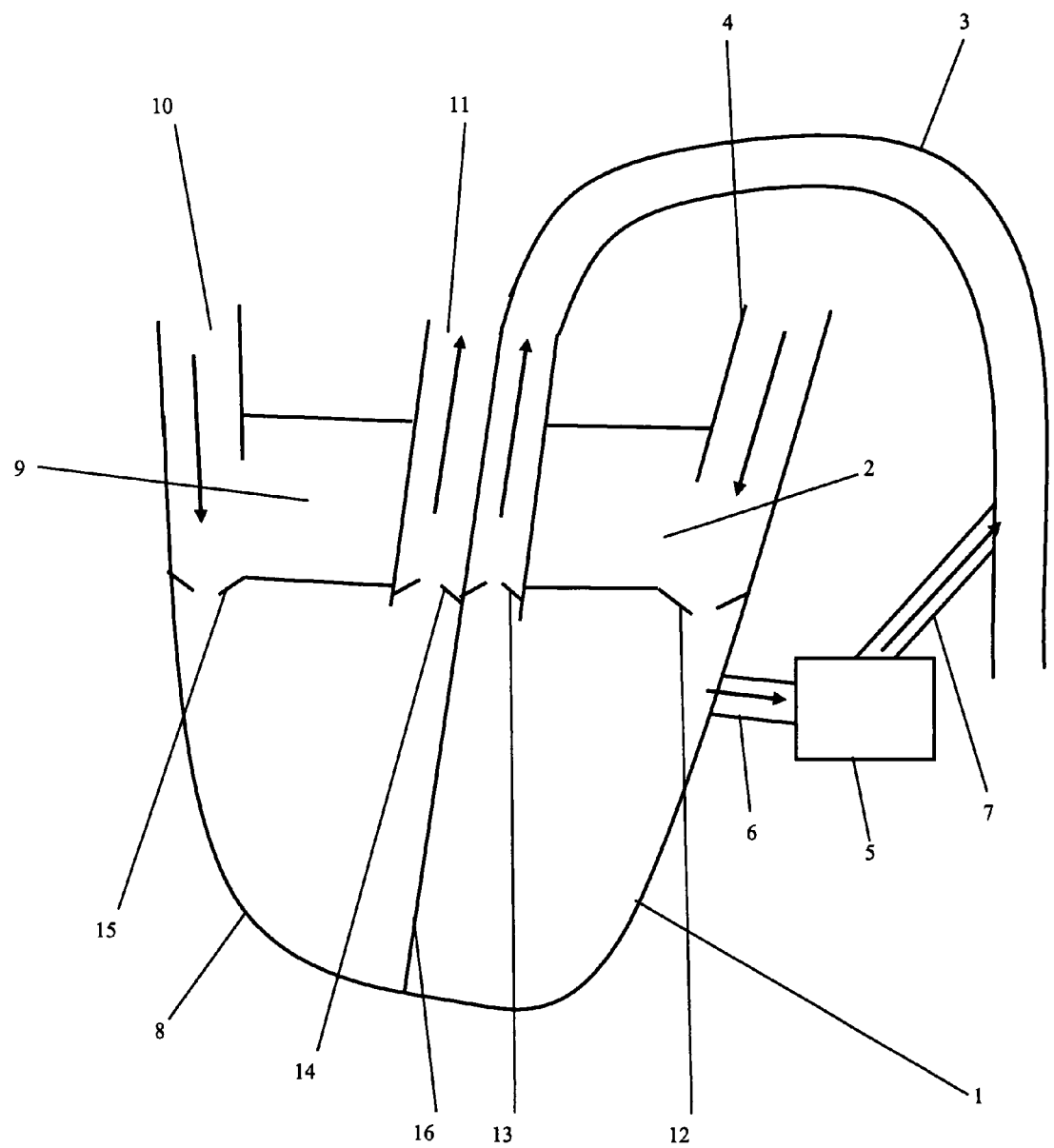
FIG. 1 depicts a schematic view of an example of the prior art.

An example of a prior art arrangement or system is depicted in FIG. 1. This system includes: a rotary blood pump 5 connected so as to assist or supplement the circulatory flow of a patient.

The schematic image of the heart depicts: the left ventricle 1; left atrium 2; aorta 3; pulmonary vein 4; pulmonary artery 11; superior vena cava 10; right atrium 9; right ventricle 8; and the intraventricular septal wall 16. The left ventricle 1 includes a mitral valve 12 and an aortic valve 13. The right ventricle 8 includes a tri-cuspid valve 15 and a pulmonic valve 14. For simplicity, none of the coronary arteries or veins have been included within the accompanying figures. For purposes of this specification references to the left side of the heart include: the left ventricle 1; left atrium 2; mitral valve 12; aortic valve 13; septum 16 and left atrial appendage (not shown).

In FIG. 1, a rotary blood pump 5 is connected to the apex of the left ventricle 1 by way of cannulae, one of which is inserted into a surgical hole that has been bored into said apex. An inflow cannula 6, which has been inserted within said cored hole, functions as a first cannula to supply blood from the left ventricle 1 to the rotary blood pump 5. The rotary blood pump 5 pumps the blood from the inflow cannula 6 to the outflow cannula 7, which functions as a second cannula. The outflow cannula 7 is attached to a descending portion of the aorta 3. This attachment may be achieved by boring a hole in the aorta 3 and securing by stitching the outflow cannula 7.

One of the main disadvantages with the example system depicted in FIG. 1, is that the left ventricle 1 may experience relatively negative blood pressures sufficient to reduce the pumping volume of the left ventricle 1 or may lead to a suction event occurring.

Additionally, this prior art system fails to adequately respond to blood pressure changes in the atria or ventricles, when the pump is in use.

Additionally, it is common for patients with late stage congestive heart failure to also suffer from hypertrophic cardiomyopathy. This is a situation where the wall in at least one chamber of the heart thickens and as a result the cavity space within said chamber narrows. This is particularly problematic in situations where the thickening has affected the wall of the left ventricle 1. As the wall of the heart thickens and the cavity space narrows, the pumping efficiency of the left ventricle 1 is compromised and risk of suction events occurring is greatly increased.

Figure 2:
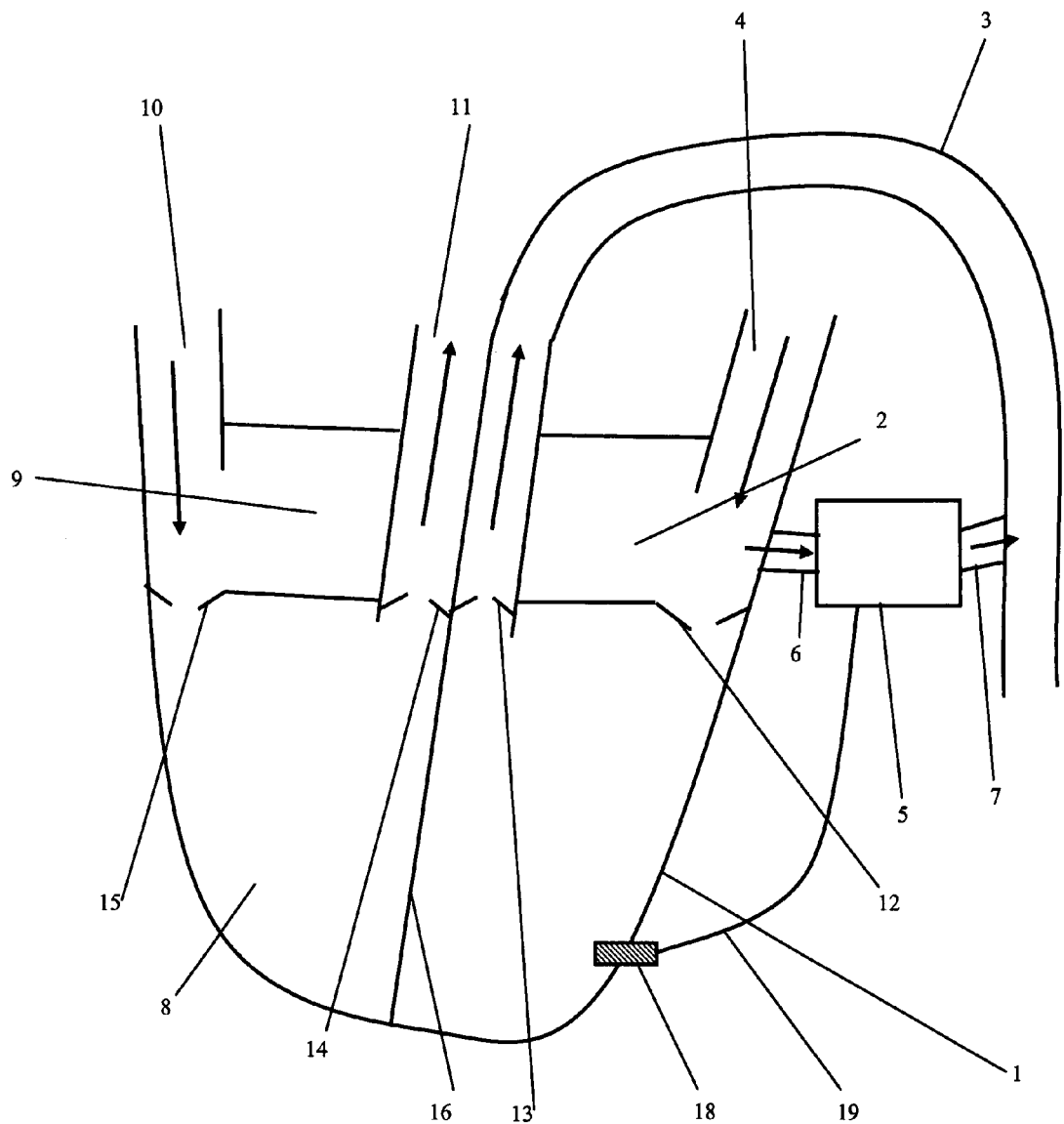
FIG. 2 depicts a schematic view of a first embodiment of the present invention.

A first preferred embodiment of the present invention is depicted in FIG. 2. The first embodiment shows a rotary blood pump 5 connected between the left atrium 2 and an aorta 3. Preferably, a hole is surgically cored in the left atrium 2 and an inflow cannula 6 is inserted within said hole. The outflow cannula 7 is anatomised to the aorta 3. The inflow cannula 6 may also alternatively be mounted on and through the left atrial appendage (not shown) and extend through into the chamber of the left atrium 2.

This arrangement of the first preferred embodiment allows the rotary blood pump 5 to be in fluid communication with the left atrium 2 and the aorta 3. Blood flows preferably through the natural heart via the left atrium 2 and the left ventricle 1 into the aorta 3 but also in parallel via the rotary blood pump 5.

Due to the nature and normal action of left atrium 2, wherein pumping is relatively low compared to the left ventricle, the rotary blood pump 5 automatically fills during diastole. Because of the limited pumping of the left atrium 2, the left atrium 2 tends not to collapse or occlude when the rotary blood pump 5 is operating. In the aforementioned prior art example, the left ventricle 1 is prone to collapse during the operation the rotary blood pump 5, particularly in situations where the heart is weakened or the pumping rate of the rotary blood pump 5 is comparably high.

Furthermore, the first preferred embodiment of the present invention may also include an implantable pressure sensor 18, which is preferably mounted in or on the inner wall of the left side of the heart. Specifically, in respect of the first preferred embodiment depicted in FIG. 2, the pressure sensor 18 is mounted through the myocardial tissue into the chamber of the left ventricle 1. Thereby, the pressure sensor 18 measures the blood pressure within the left ventricle 1. Typically, blood pressures within the chambers of the heart generally fluctuate depending the stage of the cardiac cycle that the heart is instantaneous experiencing.

The blood pressure sensor 18 preferably feedbacks data and information pertaining the blood pressure within the chamber implanted either directly to the rotary blood pump 5 (as shown in FIG. 2) or to a controller that is operating the pump 5. The controller (not shown) may adjust the pumping speed "set-point" of the rotary blood pump 5, and the rotary blood pump 5 then responds by adjusting to the instructed speed set-point. Generally, the information received from the blood pressure sensor 18 is a specialised implanted transducer with a high biocompatibility and low relatively drift in terms of data sensitivity. The information from the pressure sensor 18 is transmitted along wires 19 to the pump 5 or a controller (not shown). Preferably, the controller may be able to vary the speed as the heart beats and so regulate pressure over the cardiac cycle (rather than just maintain a static pressure within limits). This would thereby match the pumping speed to a heart rate profile.

The pressure sensor 18 may also include a wireless data transmission system, using methods including radio waves, ultrasonic waves, and optical signaling, which may remove the need for wires 19 to connect to the pump 5 or controller rather the transmission may be achieved using a standard wireless protocol including, but not limited to, Bluetooth™ wireless technology.

Preferably, the blood pressure sensor 18 may be secured in situ by the use of bio-glue or sutures.

Figure 3:
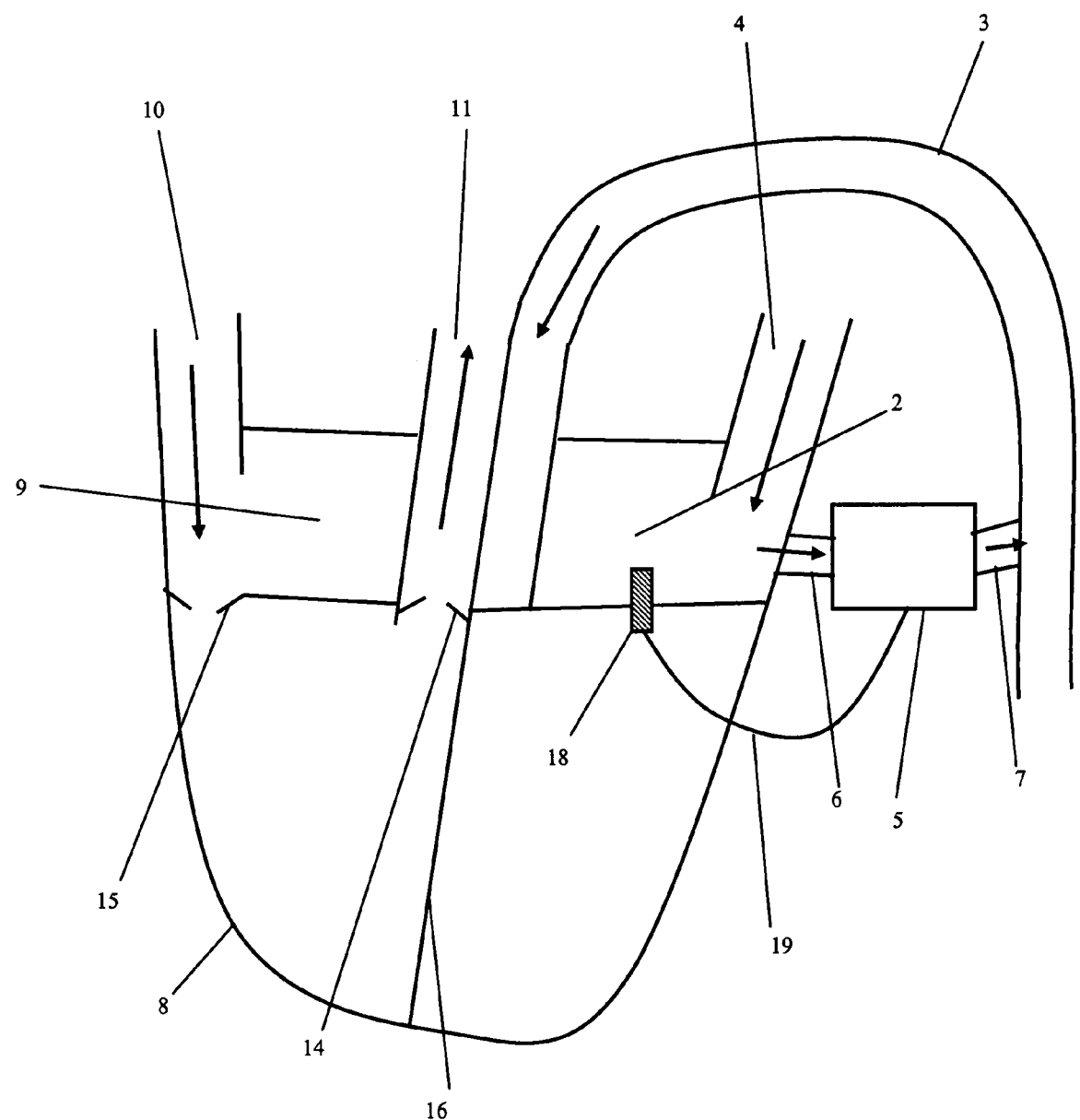
FIG. 3 depicts a schematic view of a second embodiment.

The second preferred embodiment of the present invention depicted in FIG. 3 is substantially similar to the first embodiment and a similar numbering system has been adopted. The rotary blood pump 5, in this embodiment, also connects the left atrium 2 to the aorta 3 via the use of cannulae 6 & 7. However, the left ventricle 1 has been surgically isolated from the circulation by surgically closing or occluding the aortic valve 13 and the mitral valve 12.

In instances where the patient's heart is substantially weakened, the rotary blood pump 5 may be providing a majority of the physical work needed to pump the blood and the left ventricle 1 may be experiencing low or non-existent blood flow and as a result the left ventricle 1 may experience blood clot formation, which is preferably avoided. Thus the isolation of the ventricle from the circulation will prevent these clots from entering the circulation.

In this second preferred embodiment of the present invention, the blood pressure sensor 18 is mounted through the left atrial wall in the left atrium 2. The blood pressure sensor 18 being mounted through the left atrial wall rather than the left ventricular wall (as per the first embodiment) allows the sensor to accurately determine left atrial pressure which is a better estimate of diastolic pressures experienced by the heart.

Figure 5:
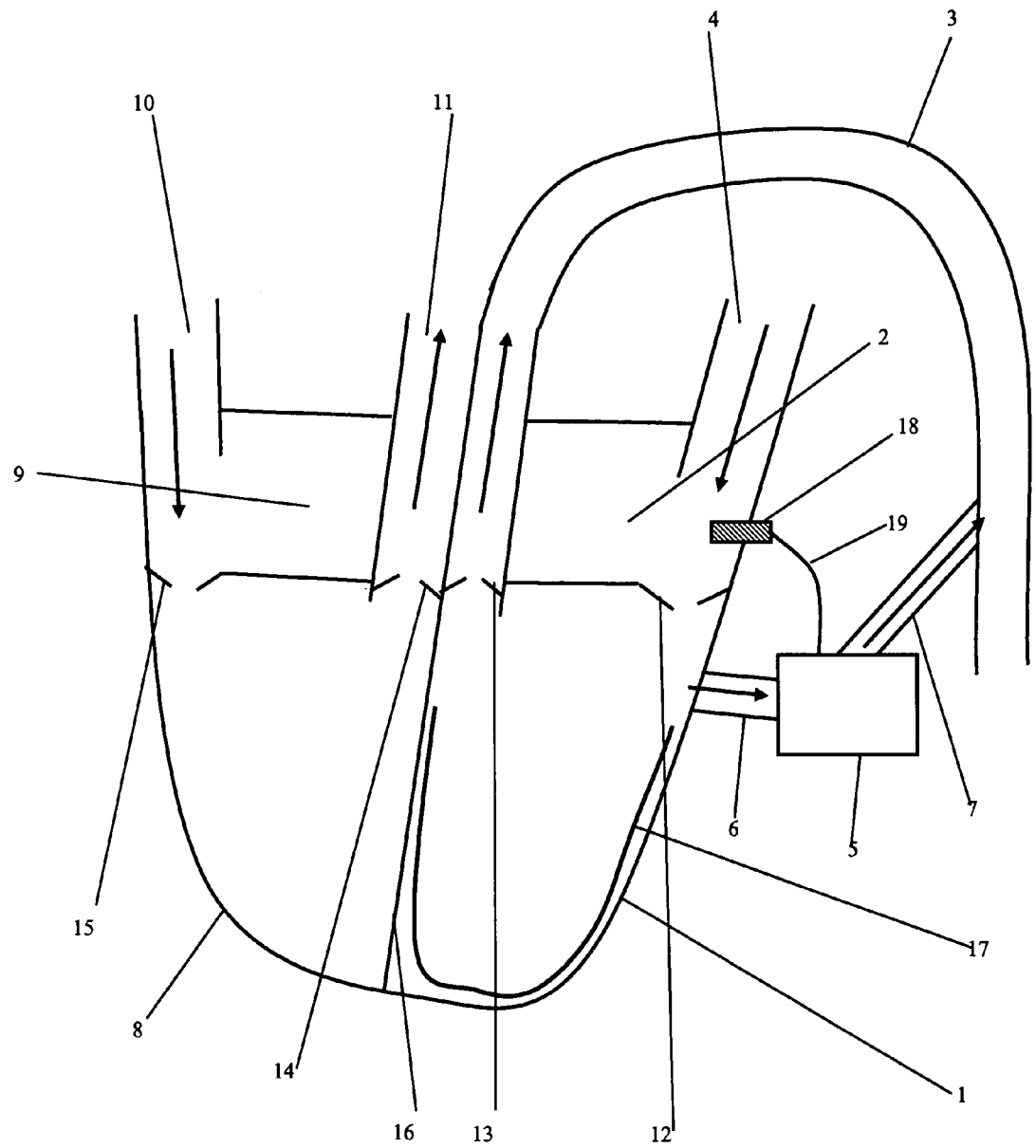
FIG. 5 depicts a schematic view of a third embodiment.

The third preferred embodiment of the present invention, as depicted in FIG. 5, includes a rotary blood pump 5 connected between the left ventricle 1 and the aorta 3. However, in this embodiment, the left ventricle 1 may be stented to maximise the volume and area within the left ventricle 1. Preferably, the stent 17 may apply sufficient pressure to the inner walls of the left ventricle 1 to be pushed away from each other whilst still allowing the left ventricle 1 to contract to facilitate its basic pumping motion. Ideally, the stent 17 would not impair the pumping function of the left ventricle 1 but rather may further allow for a means of preventing ventricular collapse or a suction event induced by the continuous pumping action of the rotary blood pump 5.

Preferably, the stent 17 may constructed of biocompatible polymer including but not limited to PEEK or a biocompatible alloy including but not limited to Titanium alloys or Nitinol. However, the stent 17 must be able to bias the walls away from each other whilst simultaneously being able to be deflected or deformed by the normal pumping contractions of the heart. Also, the stent 17 may include a perforated surface to make implantation easier.

Additionally, the stent 17 may be applied to other portions or chambers of the natural heart to prevent full or partial collapse of said chambers or portions including, but not limited to, the left atrium 2. Thereby the stent 17 may be also applied to the aforementioned first and second embodiments of the present invention.

Figure 4:
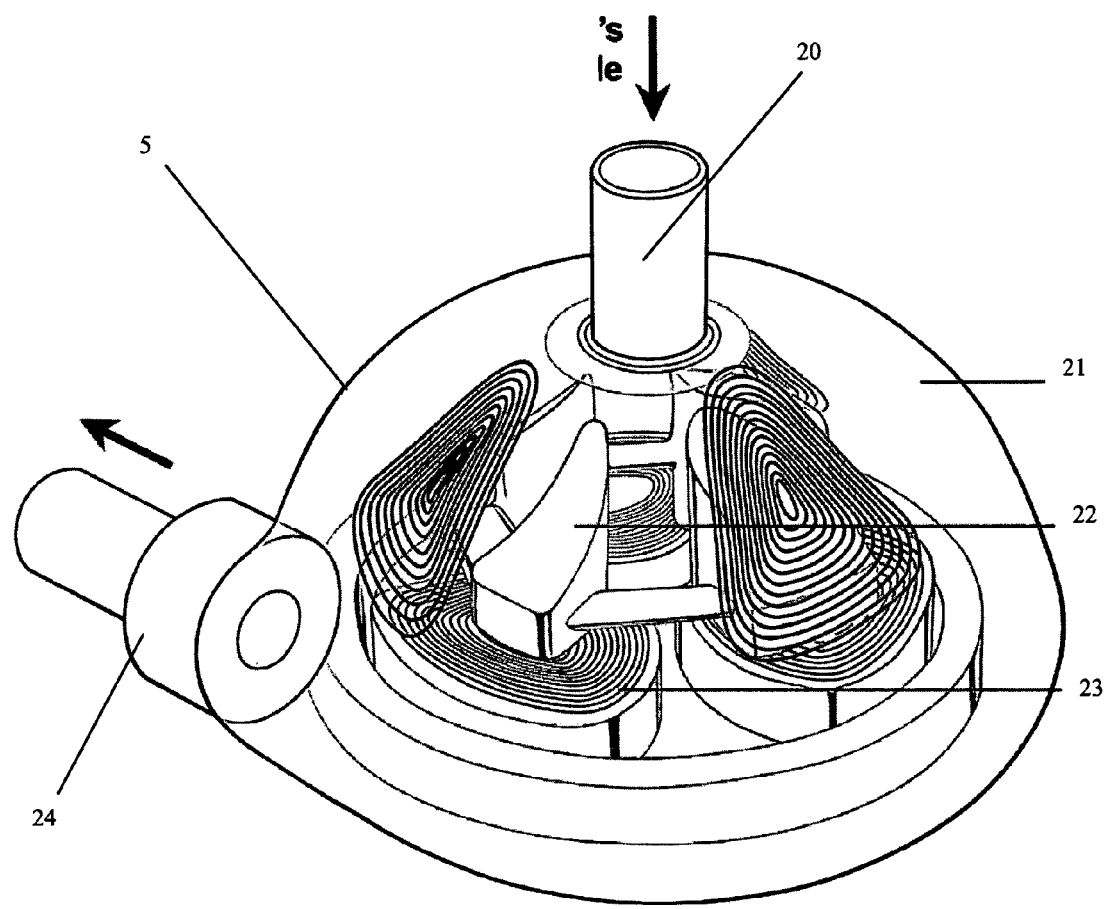
FIG. 4 depicts a more detailed transparent view of an example of a rotary blood pump for use with any of the embodiments.

The preferred rotary blood pump 5 to be used with all of the embodiments of the present invention is depicted in FIG. 4. The preferred rotary blood pump 5 is a centrifugal type blood pump wherein blood enters through the inlet header 20, which is connected to the inflow cannula 6, and exits through the outlet header 24, which is connected to an outflow cannula 7.

Preferably, the blood pump 5 includes an impeller 22 mounted for rotation within a cavity within the housing 21. During operation of the blood pump 5, the impeller 22 rotates and pushes the blood from the inlet to the exit using centrifugal force impacted by the four blades of the impeller 22. Preferably, the blades of impeller 22 include embedded and sealed permanent magnets that interact with wire coils 23 mounted within the housing 21. When the three sets of wire coils 23 are sequentially energised, the impeller 22 is magnetically urged to rotate.

Furthermore, the impeller 22 preferably includes a hydrodynamic bearing surface on the outer surfaces of the blades. This hydrodynamic bearing surface forms a wedge shaped restriction between the outer surface of the blade and the inner wall of the housing. The shape and configuration of the wedge shaped restriction provide a thrust force away from the housing and as the bearing surfaces are positioned on all blades. The resultant effect is to passively suspend the impeller 22 during rotation. Thereby the blood pump 5 depicted in FIG. 4 preferably does not include valves nor mechanical pivot bearings and as such removes points or areas of stagnation or low flow thereby preventing or limiting haemolysis or blood clotting.

Generally, the blades of impeller 22 have a shark-fin like configuration resembling a general triangular shape as depicted in FIG. 4. Preferably, this type of blade shape limits or prevents further blood damage as blood is pumped though the housing 21.

The above descriptions detail only some of the embodiments of the present invention. Modifications may be obvious to those skilled in the art and may be made without departing from the scope and spirit of the present invention.

The invention claimed is:

1. A pumping system for assisting the circulatory system of a patient, comprising:
    a rotary flow blood pump by a first cannula connected to a portion of the left side of the heart and a second cannula connected to the aorta;
    a pressure sensor for providing blood pressure measurements by mounting the pressure sensor in or on an inner wall of the left side of the heart; and
    a controller in communication with the pump, wherein the controller is configured to vary the speed of the pump over a cardiac cycle to thereby match a pumping speed to a heart rate profile based upon blood pressure measurements provided by the pressure sensor.

2. The pumping system of claim 1, wherein the pump is capable of maintaining a predetermined blood pressure profile and range within the left atrium based on feedback received from the pressure sensor.

3. The pumping system of claim 1, wherein the pump is capable of maintaining a predetermined blood pressure profile and range within the left ventricle based on feedback received from the pressure sensor.

4. The pumping system of claim 2, wherein the pump is configured to maintain a predetermined blood pressure profile and range when the pressure sensor is mounted in the left atrium or the left atrial appendage.

5. The pumping system of claim 3, further including a stent adapted for supporting the left side of the heart to prevent or limit collapse.

6. The pumping system of claim 1, wherein the pressure sensor provides feedback directly to the pump.

7. The pumping system of claim 1, wherein the pressure sensor provides feedback directly to the controller.

8. The pumping system of claim 1, wherein the pump is a centrifugal type blood pump.

* * * * *